US012478507B1

(12) United States Patent
Lu et al.

(10) Patent No.: US 12,478,507 B1
(45) Date of Patent: Nov. 25, 2025

(54) DRUG DELIVERY PART FOR VISUAL EAR PICKING STICK

(71) Applicant: HEIFENG ZHIZAO (SHENZHEN) TECHNOLOGY CO., LTD, Guangdong (CN)

(72) Inventors: Yichun Lu, Guangdong (CN); Geyan Yu, Guangdong (CN); Bicheng Dai, Guangdong (CN)

(73) Assignee: HEIFENG ZHIZAO (SHENZHEN) TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 18/818,896

(22) Filed: Aug. 29, 2024

(30) Foreign Application Priority Data

Jan. 31, 2024 (CN) ......................... 202420243224.4

(51) Int. Cl.
*A61F 11/00* (2022.01)
*G06T 1/00* (2006.01)

(52) U.S. Cl.
CPC .......... *A61F 11/006* (2013.01); *G06T 1/0007* (2013.01)

(58) Field of Classification Search
CPC ............................. A61F 11/006; G06T 1/0007
USPC ............................................................ 604/19
See application file for complete search history.

(56) References Cited

U.S. PATENT DOCUMENTS

| | | | | |
|---|---|---|---|---|
| 6,706,023 | B1 * | 3/2004 | Huttner | A61M 3/0283 604/264 |
| 2006/0095066 | A1 * | 5/2006 | Chang | A61B 17/12136 606/199 |
| 2011/0301572 | A1 * | 12/2011 | Vlodaver | A61F 11/00 604/246 |

* cited by examiner

*Primary Examiner* — Phillip A Gray
(74) *Attorney, Agent, or Firm* — Daniel M. Cohn

(57) ABSTRACT

A drug delivery part for a visual ear picking stick. The visual ear picking stick includes a shell and a movement arranged in the shell. The movement includes an image acquisition component. The shell includes a holding section and a neck section which are arranged in an axial direction. The image acquisition component is mounted at one end of the neck section facing away from the holding section. The drug delivery part includes a drug bag configured to accommodate drugs and a drug bag mounting component. The drug bag mounting component is detachably connected to the drug bag. The drug bag mounting component is provided with a drug delivery head communicated to the drug bag. The drug delivery head can be located in a range of a field of view of the image acquisition component to cooperate with the image acquisition component.

10 Claims, 2 Drawing Sheets

A-A

DRUG DELIVERY PART FOR VISUAL EAR PICKING STICK

CROSS-REFERENCE TO RELATED APPLICATIONS

The application claims priority of Chinese patent application CN202420243224.4, filed on Jan. 31, 2024, which is incorporated herein by reference in its entireties.

TECHNICAL FIELD

The present disclosure relates to the technical field of ear picking equipment, and in particular, to a drug delivery part for a visual ear picking stick.

BACKGROUND

In daily life, ear canal cleaning and proper introduction of drugs are key steps in maintaining the health of the ears. Regular ear cleaning can help keep the ear canals dry and prevent ear infections. For many common ear diseases, such as otitis media and otitis externa, it is necessary to clean an affected part of the ear and treat the affected part with drug introduction.

Existing ear picking tools usually only focus on the cleaning function, but ignore drug introduction. For example, ear picking sticks have continuously innovated in function. Visual ear picking sticks with image acquisition components have been developed. The visual ear picking sticks effectively solve the problems of inadequate cleaning and cleaning injury caused by users not being able to see the situation inside the ear canal, and the cleaning function of the ear picking sticks is further improved. However, the visual ear picking sticks still do not have a drug introduction function. Traditional local drug delivery methods for ears, including using ear drops or dipping a cotton swab in ointment, not only fail to achieve precise drug delivery, but also lead to poor results or other problems due to improper control of a dosage.

SUMMARY

The embodiments of the present disclosure provide a drug delivery part for a visual ear picking stick, which can solve the problems that a visual ear picking stick cannot have functions of ear canal cleaning and drug introduction, and cannot complete local drug delivery for treating ear diseases.

In a first aspect, the embodiments of the present disclosure provide a drug delivery part for a visual car picking stick. The drug delivery part is assembled on the visual car picking stick. The visual car picking stick includes a shell and an image acquisition component connected to the shell; the shell includes a holding section and a neck section which are arranged in an axial direction; the drug delivery part includes: a drug bag, configured to accommodate drugs; and a drug bag mounting component, detachably connected to the drug bag and configured to be detachably connected to the shell; the drug bag mounting component includes a drug delivery head communicated to the drug bag; and the drug delivery head is located in a range of a field of view of the image acquisition component to deliver a drug to an affected part of the car.

In the drug delivery part of the visual car picking rod provided in this embodiment of the present disclosure, the drug bag mounting component detachably mounts the drug bag on a main body, so that it is convenient for a user to selectively mount and replace the drug delivery part according to a usage scenario. This greatly improves the portability of a drug delivery assembly. In addition, the drug bag mounting component is provided with the drug delivery head arranged in the range of the field of view of the image acquisition component, which facilitates a user to clearly observe the environment in the car and control the drug delivery head to precisely delivery a drug to the affected part in the car, thereby improving the operability of the drug delivery part.

In some embodiments, the drug bag mounting component includes: a first mounting portion, configured to be detachably connected to the holding section, and a second mounting portion, configured to be connected to the neck section, wherein one end of the second mounting portion is connected to the first mounting portion, and the other end is connected to the drug delivery head; the first mounting portion is mounted behind the holding section; and the drug delivery head is arranged at one end or on one side of the neck section facing away from the holding section, so that the drug delivery head is located in the range of the field of view of the image acquisition component.

In some embodiments, the first mounting portion is provided with an accommodating groove, and an exposure opening communicated to the accommodating groove; after the first mounting portion is mounted behind the holding section; at least a portion of the holding section is located in the accommodating groove; a drug bag accommodating chamber is formed between the first mounting portion and the holding section; the drug bag is stored in the drug bag accommodating chamber; and at least a portion of the drug bag is exposed through the exposure opening.

The above scheme has the beneficial effects that through the cooperation between the first mounting portion and the holding section, the drug bag can be quickly and conveniently mounted and removed. Meanwhile, the design of the exposure opening facilitates a user to press the drug bag to deliver a drug to the affected part of the car.

In some embodiments, the drug bag includes: a pressure-bearing portion, configured to bear a pressure to deliver a drug and exposed through the exposure opening; and a fixed portion, arranged at an edge of the pressure-bearing portion, clamped between the first mounting portion and the holding section, and stored in the drug bag accommodating chamber.

The above scheme has the beneficial effects that the arrangement of the fixed portion ensures the stability of the pressure-bearing portion, thus avoiding displacement or falling of the pressure-bearing portion during drug delivery, and further improving the safety of use. A user can control the dosage of the drug bag by applying a pressure to the pressure-bearing portion, making the drug delivery process more precise.

In some embodiments, the first mounting portion is configured to cooperate with one end of the holding section facing away from the neck section, facilitating holding and pushing the pressure-bearing portion to deliver a drug to the affected part of the car.

The above scheme has the beneficial effects that the first mounting portion cooperates with the end of the holding section facing away from the neck section, so that the drug bag is mounted at the end of the holding section away from the neck section. When a user holds the visual car picking stick for drug introduction, the user can grasp the shell and push the pressure-bearing portion with the area between the thumb and the index finger to deliver a drug to the affected part of the car.

In some embodiments, the first mounting portion is configured to cooperate with one end of the holding section close to the neck section, facilitating pressing the pressure-bearing portion to deliver a drug to the affected part of the car.

The above scheme has the beneficial effects that the first mounting portion cooperates with the end of the holding section close to the neck section, so that the drug bag is mounted at the end of the holding section close to the neck section. When a user holds the visual car picking stick for drug introduction, the user can pinch the shell and press the pressure-bearing portion with a finger to deliver a drug to the affected part of the car.

In some embodiments, the drug delivery part for the visual car picking stick further includes: a drug guide tube; and one end of the drug guide tube is communicated to the drug bag, and the other end is communicated to the drug delivery head.

In some embodiments, the drug bag is detachably connected to the drug guide tube, and the drug guide tube is fixedly connected to the second mounting portion; or, the drug guide tube and the drug bag are of integrated structures, and the drug guide tube is detachably connected to the second mounting portion.

In some embodiments, the second mounting portion is mounted behind the neck section; a guide tube accommodating chamber is formed between the second mounting portion and the neck section; and the guide tube accommodating chamber is communicated to the drug bag accommodating chamber and is configured to accommodate the drug guide tube.

The above scheme has the beneficial effects that on the one hand, the second mounting portion in the present disclosure cooperates with the neck section to form the guide tube accommodating chamber, which can ensure the stability of the drug guide tube and avoid displacement or falling of the drug guide tube during the drug delivery. On the other hand, through semi-enclosed mounting, the second mounting portion and the drug guide tube can tightly abut against the neck section to avoid injury to the car canal caused by ribs of the drug delivery tube, so that the drug delivery process is more comfortable and convenient.

In some embodiments, the drug delivery head includes: a spherical portion, provided with a drug delivery nozzle; and a tubular portion, wherein two ends of the tubular portion are connected to the second mounting portion and the spherical portion; the tubular portion is provided with a drug delivery runner; and two ends of drug delivery runner are respectively communicated to the drug guide tube and the drug delivery nozzle.

The embodiments of the present disclosure provide the drug delivery part for the visual ear picking stick. The drug delivery part can be directly used in conjunction with the visual car picking stick: The drug bag is detachably mounted on the shell of the visual car picking stick through the drug bag mounting component, and the drug bag mounting component is provided with the drug delivery head that can be located in the range of the field of view of the image acquisition component. Through the cooperation of the drug bag, the drug bag mounting component, and the image acquisition component, a visual operation of drug delivery to the affected part of the car is achieved.

BRIEF DESCRIPTION OF THE DRAWINGS

In order to explain the technical solutions of the embodiments of the present disclosure more clearly, the following will briefly introduce the accompanying drawings used in the embodiments. Apparently, the drawings in the following description are only some embodiments of the present disclosure. Those of ordinary skill in the art can obtain other drawings based on these drawings without creative work.

DETAILED DESCRIPTION OF THE EMBODIMENTS

In order to make the aims, technical solution and advantages of the present disclosure will be clearly, the present disclosure is further described below in combination with accompanying drawings and implementations. It should be understood that the specific embodiments described herein are intended only to explain the present disclosure and are not intended to define the present disclosure.

In response to the technical problem of limited use of a visual ear picking stick in the prior art, which does not consider treatment needs of ear diseases, the present disclosure provides a drug delivery part for a visual ear picking stick. Through the cooperative use of the drug delivery part and the visual ear picking stick, integrated and visualized operations of ear canal cleaning and drug introduction are achieved, so that a user does not need to use other tools for assistance during treatment, thereby improving the functional diversity and convenience of the visual ear picking stick.

Figure 1:
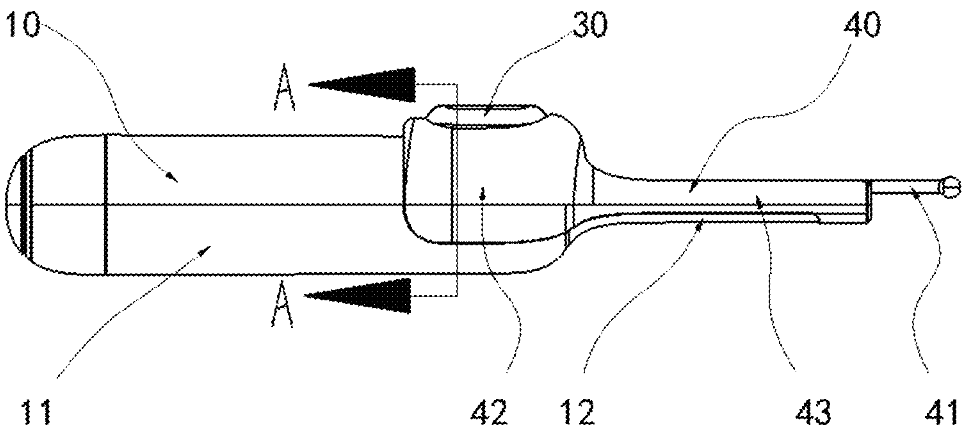
FIG. 1 is a schematic diagram of a visual ear picking stick and a drug delivery part in the present disclosure.
Figure 2:
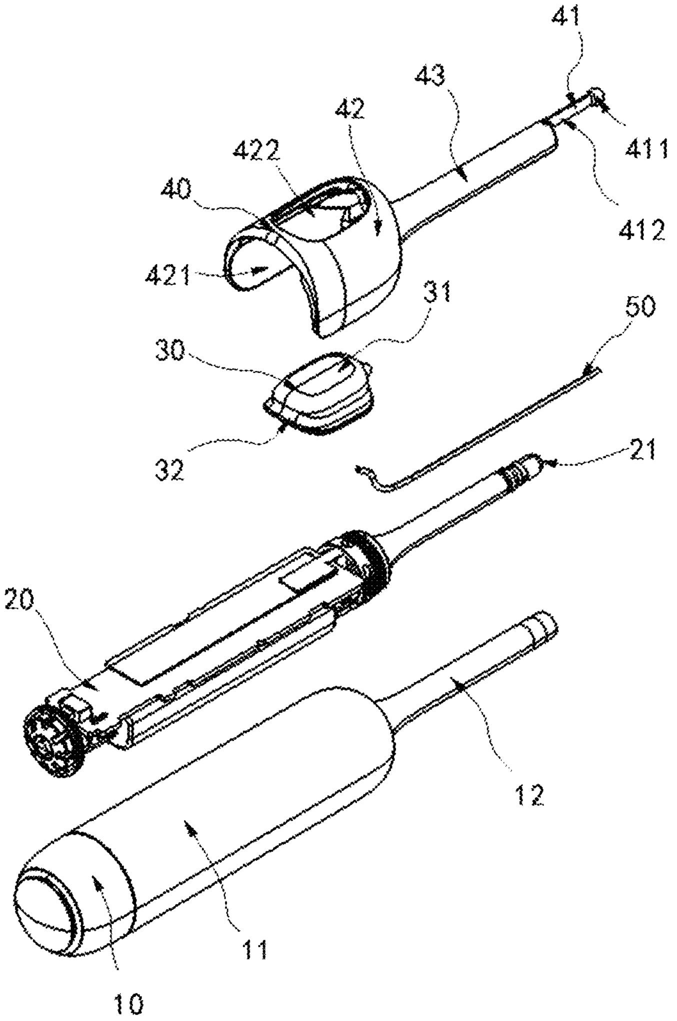
FIG. 2 is an exploded diagram of a visual ear picking stick and a drug delivery part in the present disclosure.

Referring to FIG. 1 and FIG. 2, FIG. 1 is a schematic diagram of a visual ear picking stick and a drug delivery part, and FIG. 2 is an exploded diagram of a visual ear picking stick and a drug delivery part. The visual ear picking stick includes a shell 10 and a movement 20 arranged in the shell 10. The movement 20 includes an image acquisition component 21, and the shell 10 includes a holding section 11 and a neck section 12 which are arranged in an axial direction. The image acquisition component 21 is mounted at one end of the neck section 12 facing away from the holding section 11. It can be understood that during use, the end of the neck section 12 facing away from the holding section 11 is configured to be put into the ear, and a functional component of the visible ear picking stick, such as an ear pick, is mounted at the end of the neck section 12 facing away from the holding section 11 too, and cooperates with the image acquisition component 21 to capture images in the ear and achieve ear cleaning.

As shown in FIG. 2, in this embodiment, the drug delivery part for the visual ear picking stick includes a drug bag 30, a drug bag mounting component 40, and a drug guide tube 50.

Further, the drug bag 30 is configured to accommodate drugs, and the drug bag 30 includes a pressure-bearing portion 31 configured to bear a pressure to deliver a drug, and a fixed portion 32 arranged at an edge of the pressure-bearing portion 31. The pressure-bearing portion 31 is provided with a drug storage chamber configured to accommodate drugs, and the fixed portion 32 is provided with a drug outlet communicated to the drug storage chamber. It can be understood that during use, a user can press the pressure-bearing portion 31 to drive the drugs in the drug storage chamber to flow out through the drug outlet.

Figure 3:
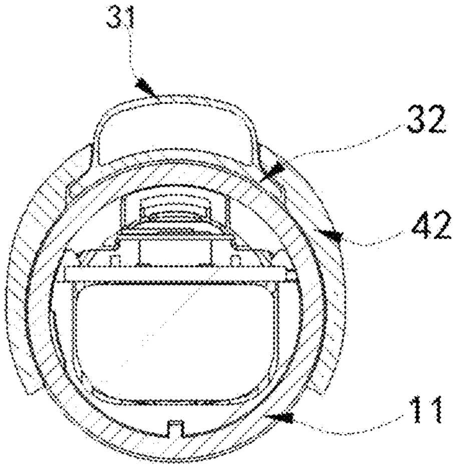
FIG. 3 is a sectional diagram of a drug delivery part for a visual ear picking stick in direction A-A in the present disclosure.

Referring to FIG. 1 to FIG. 3, FIG. 3 is a sectional diagram of a drug delivery part for a visual ear picking stick in direction A-A. In the embodiments of the present disclosure, the drug bag mounting component 40 is provided with a drug delivery head 41, a first mounting portion 42, and a second mounting portion 43 which are communicated to the drug bag 30. One end of the second mounting portion 43 is connected to the drug delivery head 41, and the other end is connected to the first mounting portion 42. The drug bag mounting component 40 is configured to detachably mount the drug bag 30 on the holding section 11, and the drug delivery head 41 can be located in a range of a field of view of the image acquisition component 21 to cooperate with the image acquisition component 21 to deliver a drug to an affected part of the ear.

Figure 4:
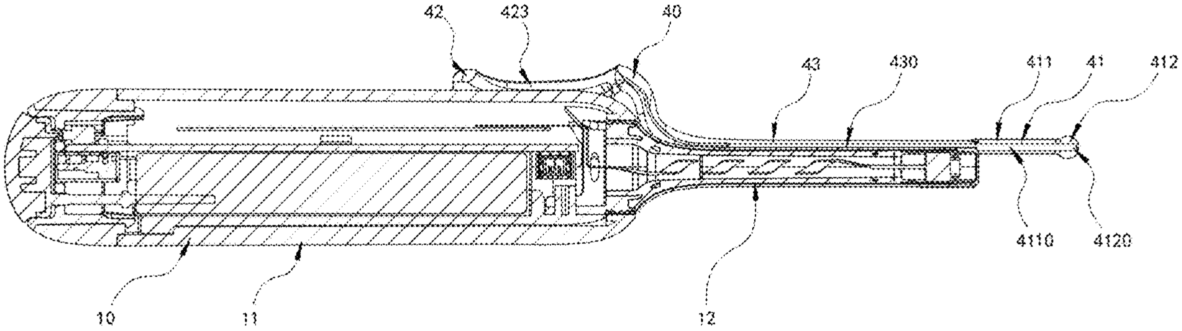
FIG. 4 is a sectional diagram after a drug bag mounting component is detachably connected to a shell in the present disclosure.

Referring to FIG. 2 to FIG. 4, FIG. 4 is a sectional diagram after a drug bag mounting component 40 is detachably connected to a shell 10. Specifically, in the drug bag mounting component 40, the first mounting portion 42 is arranged in a manner of corresponding to the holding section 11 and is mounted on the holding section 11 in a semi-enclosed manner. The first mounting portion 42 is provided with an accommodating groove 421 and an exposure opening 422 communicated to the accommodating groove 421. The holding section 11 is located in the accommodating groove 421 and forms a drug bag accommodating chamber 423 with the first mounting portion 42. The drug bag 30 is stored in the drug bag accommodating chamber 423, and a portion of the drug bag 30 is exposed through the exposure opening 422. Specifically, the fixed portion 32 is sandwiched between the first mounting portion 42 and the holding section 11 and stored in the drug bag accommodating chamber 423, and the pressure-bearing portion 31 is exposed out of the exposure opening 422. It can be understood that the arrangement of the fixed portion 32 ensures the stability of the pressure-bearing portion 31, thereby avoiding displacement and falling of the pressure-bearing portion 31 in a drug delivery process.

As a feasible implementation, the first mounting portion 42 cooperates with one end of the holding section 11 away from the neck section 12, so that the drug bag 30 is mounted at one end of the holding section 11 away from the neck section 12. When a user holds the visual ear picking stick for drug introduction, the user can grasp the shell 10 and push the pressure-bearing portion 31 with the area between the thumb and the index finger to deliver a drug to the affected part of the ear.

As another feasible implementation, the first mounting portion 42 cooperates with one end of the holding section 11 close to the neck section 12, so that the drug bag 30 is mounted at the end of the holding section 11 close to the neck section 12. When a user holds the visual ear picking stick for drug introduction, the user can pinch the shell 10 and press the pressure-bearing portion 31 with a finger to deliver a drug to the affected part of the ear.

In the drug bag mounting component 40, the first mounting portion 42 is mounted behind the holding section 11; and the drug delivery head 41 is arranged at one end of the neck section 12 facing away from the holding section 11, so that the drug delivery head 41 is located in the range of the field of view of the image acquisition component 21, which ensures that a user can clearly observe the affected part in the ear canal and precisely delivery a drug.

In some embodiments, the drug delivery head 41 includes a spherical portion 411 and a tubular portion 412. Two ends of the tubular portion 412 are respectively connected to the second mounting portion 43 and the spherical portion 411. The spherical portion 411 is provided with a drug delivery nozzle 4110. It can be understood that after the drug delivery part is assembled on the visual ear picking stick, rotating the shell 10 will cause a change in the orientation of the drug bag 30, which is not conducive to drug delivery. Therefore, limited by the position of the drug bag 30 and the narrow space inside the ear, the drug delivery head 41 has a small adjustment range. In this embodiment, to ensure that the drug can cover the affected part, the spherical portion 411 is designed in the drug delivery head 41, and the drug delivery nozzle 4110 is provided at the spherical portion 411. The tubular portion 412 is provided with a drug delivery runner 4120, and two ends of the drug delivery runner 4120 are respectively communicated to the drug guide tube 50 and the drug delivery nozzle.

Referring to FIG. 1 to FIG. 4, in the drug bag mounting component 40, the second mounting portion 43 is arranged in a manner of corresponding to the neck section 12 and is mounted at the neck section 12 in a semi-enclosed manner; a guide tube accommodating chamber 430 is formed between the second mounting portion 43 and the neck section 12; and the guide tube accommodating chamber 430 is communicated to the drug bag accommodating chamber 423 and is configured to accommodate the drug guide tube 50. It can be understood that due to the design of the guide tube accommodating chamber 430, the stability of the drug guide tube 50 can be ensured, and displacement or falling of the drug guide tube 50 during the drug delivery can be avoided. Furthermore, injury to the ear canal caused by ribs of the drug delivery tube 50 can be avoided, so that the drug delivery process is more comfortable and convenient.

In this embodiment, one end of the drug guide tube 50 is communicated to the drug bag 30, and the other end is communicated to the drug delivery head 41. As a feasible implementation, the drug bag 30 is detachably connected to the drug guide tube 50, and the drug guide tube 50 is fixedly connected to the second mounting portion 43. In a scenario of continuous use by a single person, the structure of fixedly connected drug guide tube 50 and second mounting portion 43 is convenient for a user to replace the drug bag 30.

As another feasible implementation, the drug guide tube 50 and the drug bag 30 are of integrated structures, and the drug guide tube 50 is detachably connected to the second mounting portion 43. In a scenario of alternate use by many people, the drug guide tube 50 and the drug bag 30 are of the integrated structures, which is convenient for a user to replace the drug bag mounting component 40 and can avoid cross infections.

Further, a user can select drug guide tubes 50 with different inner diameters for drugs with different viscosities. For low-viscosity drugs, such as ear drops, a drug guide tube 50 with a small inner diameter, as well as a drug bag mounting component 40 and a drug bag 30 which are adapted to the caliber of the drug guide tube 50, can be used. It can be understood that if an inner diameter of the drug delivery nozzle in the drug bag mounting component 40 is small, under the action of surface tension, a drug can be kept being accommodated in the drug delivery part. This effectively avoids disorder of drugs and better controls the amount and speed of drug delivery. For high-viscosity drugs, such as gelatinizing agents or ointments, a drug guide tube 50 with a large inner diameter, as well as a drug bag mounting component 40 and a drug bag 30 which are adapted to the caliber of the drug guide tube 50, can be used to ensure smooth extrusion of drugs.

In general, in the drug delivery part for the visual ear picking stick of the embodiments of the present disclosure, the first mounting portion 42 and the holding section 11 can be used in conjunction with each other to quickly and conveniently mount and remove the drug bag 30. In conjunction with the situation, acquired by the image acquisition component 21, in the ear, precise drug delivery can be achieved on the affected part of the ear by moving the drug delivery head 41 and pressing the pressure-bearing portion 31 exposed out of the exposure opening 422. In the embodiments of the present disclosure, drug bag mounting positions suitable for being gripped and pushed for drug delivery and suitable for being pressed for drug delivery are designed for different usage habits. In the embodiments of the present disclosure, the second mounting portion 43 cooperates with the neck section 12 to form the guide tube accommodating chamber 430 configured to accommodate the drug guide tube.

On the one hand, the stability of the drug guide tube 50 can be ensured, and displacement or falling of the drug guide tube 50 during the drug delivery can be avoided. On the other hand, the second mounting portion 43 and the drug guide tube 50 can tightly abut against the neck section 12, which can effectively avoid injury to the ear canal caused by ribs of the drug delivery tube.

The identical or similar numerals in the accompanying drawings in this embodiment correspond to identical or similar components. In the description of the present disclosure, it should be understood that orientations or positional relationships indicated by the terms “upper”, “lower”, “left”, “right”, and the like are orientations or positional relationships as shown in the drawings, and are only for the purpose of facilitating and simplifying the description of the present disclosure instead of indicating or implying that devices or elements indicated must have particular orientations, and be constructed and operated in the particular orientations, so that these terms for describing the positional relationships in the accompanying drawings are only used for exemplary illustrations and are not construed as limiting the present disclosure. A person of ordinary skill in the art can understand the specific meanings of the above terms according to specific situations.

The foregoing description is merely illustrative of the preferred embodiments of the present disclosure and is not intended to limit the present disclosure, but it is intended that any modifications, equivalents, substitutions, and modifications made within the spirit and principles of the present disclosure be embraced within the scope of the present disclosure.

What is claimed is:

1. A drug delivery part for a visual ear picking stick, wherein the drug delivery part is assembled on the visual ear picking stick; the visual ear picking stick comprises a shell and an image acquisition component connected to the shell; the shell comprises a holding section and a neck section which are arranged in an axial direction; the drug delivery part comprises:

a drug bag, configured to accommodate drugs; and a drug bag mounting component, detachably connected to the drug bag and configured to be detachably connected to the shell, wherein the drug bag mounting component comprises a drug delivery head communicated to the drug bag; and the drug delivery head is located in a range of a field of view of the image acquisition component to deliver a drug to an affected part of the ear.

2. The drug delivery part for the visual ear picking stick according to claim 1, wherein the drug bag mounting component comprises:

a first mounting portion, configured to be detachably connected to the holding section, and a second mounting portion, configured to be connected to the neck section, wherein one end of the second mounting portion is connected to the first mounting portion, and the other end is connected to the drug delivery head;

the first mounting portion is mounted behind the holding section; and the drug delivery head is arranged at one end or on one side of the neck section facing away from the holding section, so that the drug delivery head is located in the range of the field of view of the image acquisition component.

3. The drug delivery part for the visual ear picking stick according to claim 2, wherein the first mounting portion is provided with an accommodating groove, and an exposure opening communicated to the accommodating groove;

after the first mounting portion is mounted behind the holding section; at least a portion of the holding section is located in the accommodating groove; a drug bag accommodating chamber is formed between the first mounting portion and the holding section; the drug bag is stored in the drug bag accommodating chamber; and at least a portion of the drug bag is exposed through the exposure opening.

4. The drug delivery part for the visual ear picking stick according to claim 3, wherein the drug bag comprises:

a pressure-bearing portion, configured to bear a pressure to deliver a drug and exposed through the exposure opening; and a fixed portion, arranged at an edge of the pressure-bearing portion, clamped between the first mounting portion and the holding section, and stored in the drug bag accommodating chamber.

5. The drug delivery part for the visual ear picking stick according to claim 4, wherein the first mounting portion is configured to cooperate with one end of the holding section facing away from the neck section, facilitating holding and pushing the pressure-bearing portion to deliver a drug to the affected part of the ear.

6. The drug delivery part for the visual ear picking stick according to claim 4, wherein the first mounting portion is configured to cooperate with one end of the holding section close to the neck section, facilitating pressing the pressure-bearing portion to deliver a drug to the affected part of the ear.

7. The drug delivery part for the visual ear picking stick according to claim 3, further comprising:

a drug guide tube, wherein one end of the drug guide tube is communicated to the drug bag, and the other end is communicated to the drug delivery head.

8. The drug delivery part for the visual ear picking stick according to claim 7, wherein the drug bag is detachably connected to the drug guide tube, and the drug guide tube is fixedly connected to the second mounting portion; or, the drug guide tube and the drug bag are of integrated structures, and the drug guide tube is detachably connected to the second mounting portion.

9. The drug delivery part for the visual ear picking stick according to claim 7, wherein the second mounting portion is mounted behind the neck section; a guide tube accommodating chamber is formed between the second mounting portion and the neck section; and the guide tube accommodating chamber is communicated to the drug bag accommodating chamber and is configured to accommodate the drug guide tube.

10. The drug delivery part for the visual ear picking stick according to claim 7, wherein the drug delivery head comprises:

a spherical portion, provided with a drug delivery nozzle; and a tubular portion, wherein two ends of the tubular portion are connected to the second mounting portion and the spherical portion; the tubular portion is provided with a drug delivery runner; and two ends of drug delivery runner are respectively communicated to the drug guide tube and the drug delivery nozzle.

* * * * *